United States Patent [19]

Yoshii et al.

[11] Patent Number: 5,780,026

[45] Date of Patent: Jul. 14, 1998

[54] IMMUNOMODULATING AND ANTIINFLAMMATORY AGENT

[75] Inventors: Haruo Yoshii; Yuriko Fukata, both of Katoh-gun, Japan

[73] Assignee: Nippon Zoki Pharmaceutical Co., Ltd., Osaka, Japan

[21] Appl. No.: 287,249

[22] Filed: Aug. 8, 1994

[30] Foreign Application Priority Data

Aug. 9, 1993  [JP]  Japan .................................. 5-218043

[51] Int. Cl.$^6$ .......................... A61K 35/14; A61K 35/16
[52] U.S. Cl. ................................... 424/130.1; 424/133.1;
514/2; 514/21; 514/826; 514/885; 514/887
[58] Field of Search ............................... 514/2, 21, 826,
514/885, 887; 424/130.1, 133.1

[56] References Cited

U.S. PATENT DOCUMENTS

| | | | |
|---|---|---|---|
| 4,704,273 | 11/1987 | McMichael | 424/85 |
| 4,705,685 | 11/1987 | McMichael | 424/89 |
| 4,705,687 | 11/1987 | Lau | 424/95 |
| 5,354,848 | 10/1994 | Faligiani et al. | 530/395 |
| 5,622,970 | 4/1997 | Armistead et al. | 514/315 |
| 5,639,758 | 6/1997 | Sharpe et al. | 514/278 |

FOREIGN PATENT DOCUMENTS

0 646 376 A1  4/1995  European Pat. Off. .

OTHER PUBLICATIONS

Curtis et al., *Biology*, Fifth Edition, Worth Publication; (New York) 1989 pp. 835–836.
M. Naiki et al., "Neurotropin Inhibits Experimental Allergic Encephalomyelitis (EAE) in Lewis Rats", *Int. J. Immunopharmac.*, 13(2/3), 235–243 (1991).
"Drug Evaluations Annual 1995", American Medical Association, pp. 438–445 (1995).
Goodin, "The use of immunosuppressive agents in the treatment of multiple sclerosis: A critical review", *Neurology*, vol. 41, pp. 980–985 (1991).
Higashiguchi, et al., Chemical Abstracts 112:111828b, 1990.
Getlik, et al., Chemical Abstracts 67, #5, 20482v, 1967.
Volokhovskaya, et al., Chemical Abstracts, 115:21847q, 1991.
Yoshii, et al., "Inhibitory Effect of Histamine–Added Mouse γ–Globulin On Eosinophil Accumulation Induced By Allergen In Balb/c Mice", *Japanese Journal of Allergology*, 44:567–570 (1995).
Yoshii, et al., "A New Assay System Detecting Antibody Production And Delayed–Type Hypersensitivity Responses To Trinitrophenyl Hapten In An Individual Mouse", *Int. J. Immunopharmac.*, vol. 18, No. 1, pp. 31–36, 1996.
Fujiwara, et al., "Sandwich enzyme immunoassay of tumor–associated antigen sialosylated Lewis using β–D–galactosidase coupled to a monoclonal antibody of IgM isotype", *Journal of Immunological Methods*, 112, pp. 77–83, 1988.
Burnham, "Polymers for delivering peptides and proteins", *Am J Hosp Pharm*, vol. 51, pp. 210–218, Jan. 15, 1994.
Wood, et al., Biochemistry A Problems Approach, 2nd edition, pp. 155–156, 1981.
Naiki, et al., 9th International Congress of Immunology, p. 183, abstract 1084, Jul. 23–29, 1995.
Kaneko, et al., "Role of Interleukin–5 in Local Accumulation of Eosinophils in Mouse Allergic Peritonitis," *Int. Arch Allergy Appl Immunol.*, 1991; 96:41–45.

*Primary Examiner*—Peter O'Sullivan
*Attorney, Agent, or Firm*—Fisher, Christen & Sabol

[57] ABSTRACT

In the present invention, pharmaceutical compositions containing a histamine-added gamma-globulin as an effective component are used as an immunomodulating agent, a suppressive agent for eosinophilia, and as an antiinflammatory agent. The immunomodulating action is unexpectedly different from the action of conventional immunosuppressive agents. Accordingly, the compositions are useful as a pharmaceutical agent for the therapy of diseases associated with an abnormal immune system such as chronic articular rheumatism, systemic lupus erythematosus, multiple sclerosis, etc. and various types of immunodeficiency syndromes. In addition, the pharmaceutical compositions exhibit suppressive action upon hypereosinophilicity. They may be used as a therapeutic agent for infectious diseases, parasitic diseases, respiratory diseases, autoimmune diseases and eosinophilia caused by malignant tumors. The compositions are excellent antiinflammatory agents.

11 Claims, 2 Drawing Sheets

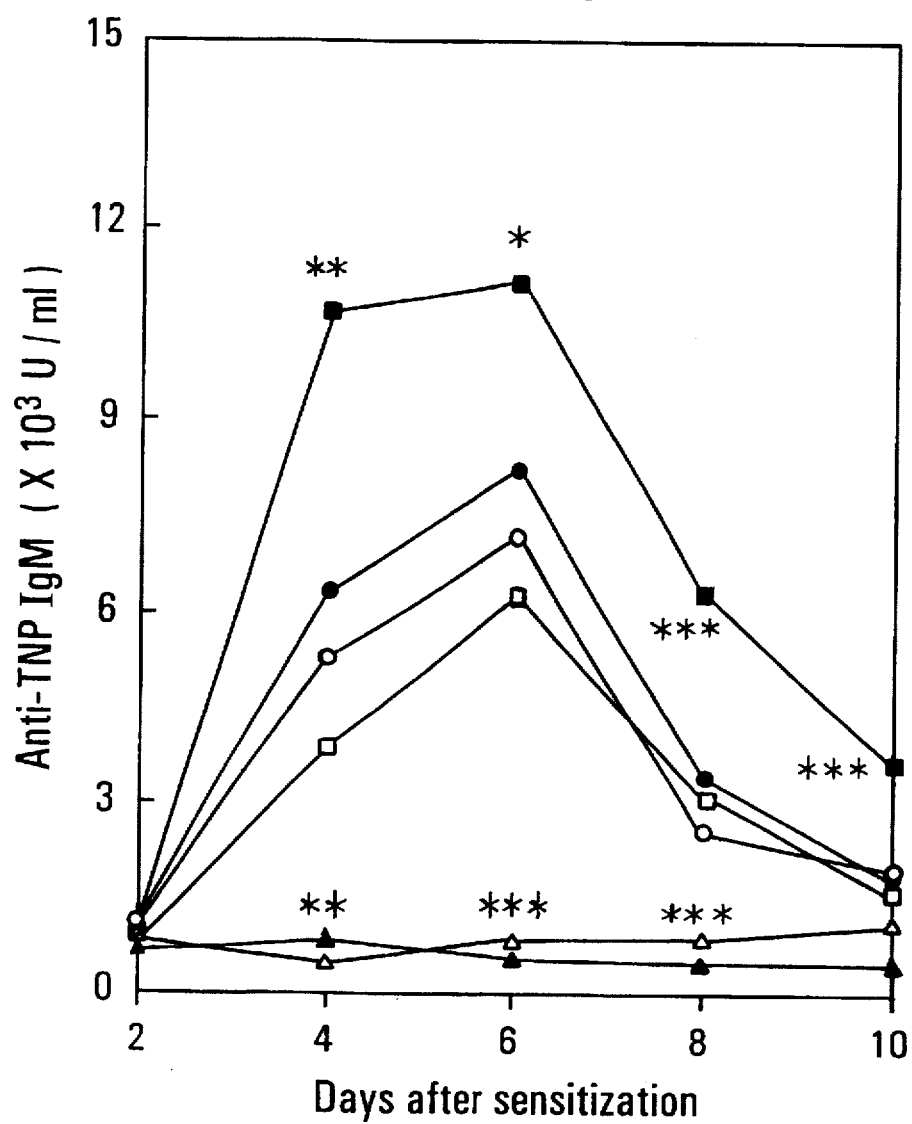

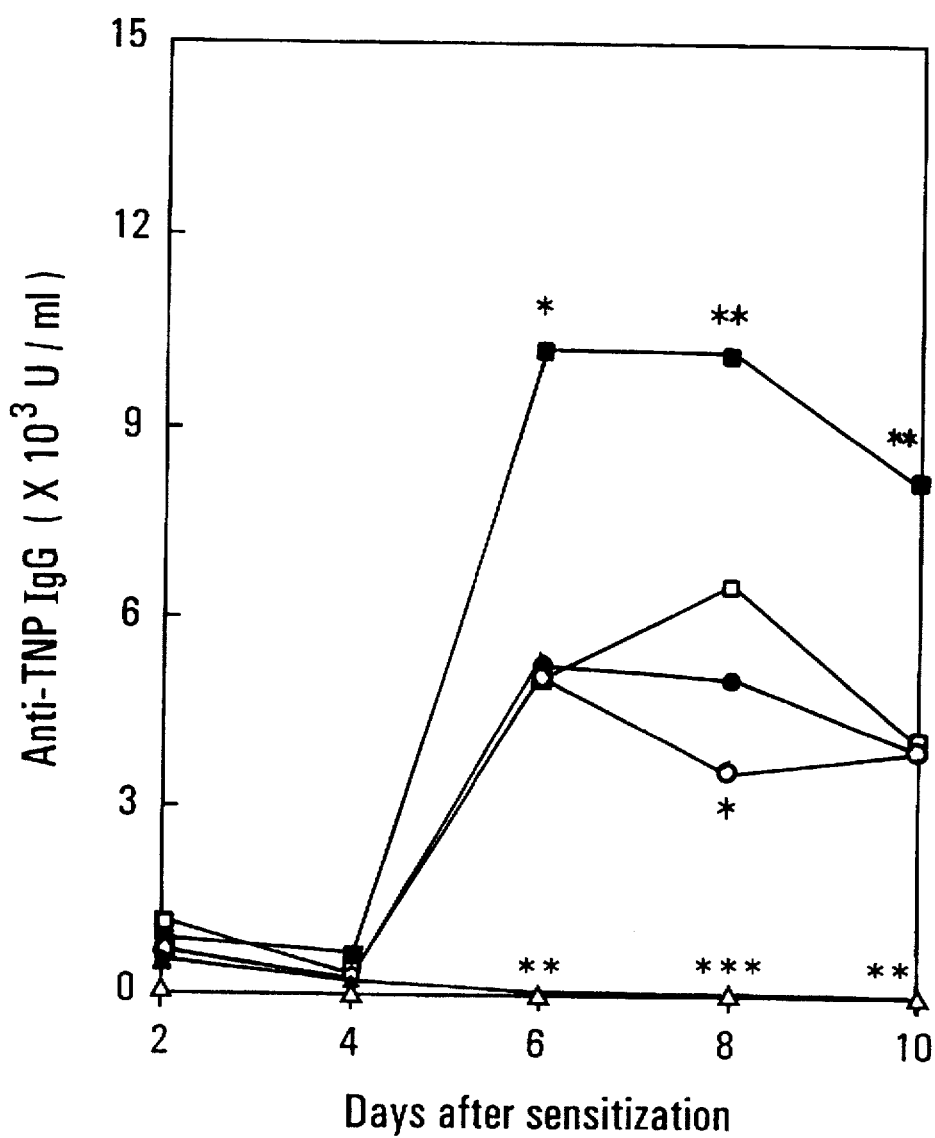

IMMUNOMODULATING AND ANTIINFLAMMATORY AGENT

FIELD OF THE INVENTION

The present invention relates to the use of a histamine-added gamma-globulin as pharmaceuticals. More particularly, it relates to an immunomodulating agent, a suppressive agent to hypereosinophilicity and an antiinflammatory agent containing the histamine-added gamma-globulin as an effective component.

BACKGROUND OF THE INVENTION

Histamine-added gamma-globulin restores histamine fixing ability which is lowered in patients suffering from allergy and asthma. It is used as an agent for nonspecific hyposensitizing therapy for bronchial asthma, allergic rhinitis and allergic skin diseases such as urticaria, chronic eczema, atopic dermatitis, etc. Histamine-added gamma-globulin also exhibits suppressive action to liberation of histamine. It does not exhibit side effects exhibited by antihistamines and adrenocortical hormones used as symptomatic remedies. It has therefore been widely used as a pharmaceutical agent with high safety.

The present inventors have found that histamine-added gamma-globulin exhibits unexpected pharmacological action including immunomodulating action, suppressive action towards hypereosinophilicity, and antiinflammatory action.

SUMMARY OF THE INVENTION

The present invention provides pharmaceutical compositions which contain histamine-added gamma-globulin in pharmaceutically effective amounts which are effective as an immunomodulating agent, a hypereosinophilicity suppressive agent, and an antiinflammatory agent. The compositions may be in the form of a liquid injection or a dry preparation which is dissolved upon use for injection. In embodiments of the present invention the compositions may be used for treatment of mammalian diseases associated with an abnormal immune system such as chronic articular rheumatism, systemic lupus erythematosus, multiple sclerosis, and immunodeficiency syndromes. Therapeutic treatment of mammalian infectious diseases, parasitic diseases, respiratory diseases, autoimmune diseases and eosinophilia caused by a malignant tumor may also be achieved with the pharmaceutical compositions. The histamine-added gamma-globulin may be made by admixing from about 1 to about 200 parts by weight gamma-globulin with about 0.01 to about 2 parts by weight of a histamine component. In preferred embodiments, from about 5 to about 50 parts by weight gamma-globulin may be combined with about 0.05 to about 0.5 parts by weight of a histamine component to obtain the histamine-added gamma-globulin.

BRIEF DESCRIPTION OF THE DRAWINGS

FIG. 1 is a graph showing the potentiating action of histamine-added gamma globulin to anti-TNP IgM antibody production.

FIG. 2 is a graph showing the potentiating action of histamine-added gamma globulin to anti-INP IgG antibody production.

DETAILED DESCRIPTION OF THE INVENTION

In the present invention histamine-added gamma-globulin is used in pharmaceutically effective amounts in immunomodulating agents, hypereosinophilicity suppressive agents, and antiinflammatory agents. The histamine-added gamma-globulin provides unexpectedly effective immunomodulating action, inhibiting action to hypereosinophilicity, and antiinflammatory action in the pharmaceutical compositions. It may be manufactured by mixing of a gamma-globulin component with a histamine component to obtain a substantially homogeneous mixture. Human gamma-globulin for use in the present invention in treating humans may be prepared from serum or from placenta plasma or the like by conventional means. The histamine component may be free histamine or a pharmacologically-acceptable salt thereof such as hydrochloride, phosphate, picrate, etc., or mixtures thereof.

In embodiments of the present invention, the histamine-added gamma-globulin may be made by admixing from about 1 to about 200 parts by weight gamma-globulin with about 0.01 to about 2 parts by weight of a histamine component. In preferred embodiments, from about 5 to about 50 parts by weight gamma-globulin may be combined with about 0.05 to about 0.5 parts by weight of a histamine component to obtain the histamine-added gamma-globulin. For example, in the manufacture of the product of the present invention, 100 to 200 mg (preferably 5 to 50 mg) of gamma-globulin may, for example, be mixed with 0.01 to 2 micrograms (preferably 0.05 to 0.5 microgram) of histamine component with conventional mixing means.

The histamine-added gamma-globulin products of the present invention are primarily administered as injections. They can be made into a pharmaceutical composition as an isotonic solution using distilled water for injection or a physiological saline solution. In its manufacture, one or more additives such as auxiliary solubilizers, isotonizing agents, stabilizers, buffers, preservatives, etc. may be used in pharmaceutically acceptable amounts in addition to the gamma-globulin component and the histamine component. Examples of the applicable additives are citric acid, sodium benzoate, glycine, sodium sulfite, sodium bisulfite, sodium pyrosulfite, sodium thiosulfate, cysteine hydrochloride, phosphates, sodium ascorbate, sodium chloride, sodium bicarbonate, etc., and mixtures thereof.

Further, the product of the present invention may be prepared as an injectable preparation which is dissolved upon actual use. Thus, each of the components may be mixed in a dry state. In another embodiment, a mixed solution may be filled in vials or the like followed by freeze-drying. In the manufacture of the dry preparation for injection, one or more fillers such as glucose, mannitol and sorbitol may be added in addition to the above-mentioned additives. An example of a dry preparation for injection is a histamine-added immunized human globulin preparation.

The present invention is illustrated by the following examples:

EXAMPLE 1

Mice were used as experimental animals in the following pharmacological tests and, accordingly, mouse gamma-globulin was used in place of human gamma-globulin. Both types of histamine-added gamma-globulin may be produced in the same manner. Thus, for the pharmacological tests on mice, a mouse gamma-globulin and histamine dihydrochloride were dissolved in distilled water in the following mixing ratios:

| Product of the Present Invention | Amount of Mouse gamma-Globulin | Amount of Histamine.2HCl |
|---|---|---|
| HG50 | 5.3 mg | 0.10 microgram |
| HG75 | 12.0 mg | 0.15 microgram |
| HG90 | 28.8 mg | 0.30 microgram |

Each solution was stirred at room temperature for two hours, freeze-dried and, upon use, dissolved by adding a physiological saline solution thereto.

Each of the HG50, HG75 and HG90 products prepared above exhibited significant effects in all of the following pharmacological tests and, accordingly, only the results obtained for HG75 will be given as representative thereof:

I. IMMUNOMODULATING ACTION

The immunomodulating action was measured using the production of an antibody specific to trinitrophenyl (TNP) and also a delayed TNP-specific hypersensitivity (DTH) reaction as targets.

(1) Preparation of Trinitrophenyl-Bonded Sheep Red Cells (TNP-SRBC).

Trinitrobenzenesulfonic acid (TNBS) was dissolved in a physiological saline solution buffered with phosphoric acid to prepare a solution (40 mg/7.0 ml; pH 7.2) and then 1 ml of sheep red cell pellets was dropped thereinto with stirring. The mixture was allowed to stand at room temperature with stirring for several times under a light-shielding state and washed with a physiological saline solution three times. Then it was centrifuged at 3,000 rpm for five minutes and made into a solution of $5\times10^9$ cells/ml using a physiological saline solution.

(2) Production of a TNP-Specific Antibody.

TNP-SRBC ($10^9$ cells) was intraperitoneally administered to male BALB/c mice of six to eight weeks age and the anti-TNP antibody in serum was measured by an enzymatic immunoassay (ELISA) using a dinitrophenyl-bovine serum albumin (DNP-BSA). The result was that a potent antibody production of anti-TNP-IgM and anti-TNP-IgG was noted having a peak on the 4th to 6th days. In the case of BALB/c nude mice having no thymus, production of antibodies of both types was rarely noted.

(3) TNP-Specific DTH Reaction.

The mice were sensitized with TNP-SRBC as described in paragraph (2) above. On the 14th day, 0.025 ml of TNB (4.7 mg/ml) was injected into the right hind paw to induce a TNP-specific DTH reaction. After 24 hours and 48 hours from the induction, the thickness of both paws was measured using a dial gauge. The difference in the thickness between the right and left paws was expressed as the intensity of the DTH reaction. The result was that, after 24 hours from the induction, a DTH reaction was clearly noted. However, in the case of BALB/c nude mice, no DTH reaction was observed at all. This measuring system for the DTH reaction can be subjected to further tests using the same mice as in the case of the antibody production system of paragraph (2) above.

(4) Measurement of the Action of the Tested Drugs.

The above-mentioned test system was used for checking the action of: (a) the histamine-added mouse gamma-globulin (150 mg/kg/day) (the product of the present invention), (b) cyclosporin A (100 mg/kg/day), (c) cyclophosphamide (100 mg/kg/day), (d) prednisolone (0.5 kg/kg/day) and (e) levamizole (5 mg/kg/day) towards the anti-TNP antibody production and to the TNP-specific DTH reaction. The drugs were administered by hypodermic injection four days from the sensitization with TNP-SRBC.

The results for the anti-TNP antibody production system is given in FIG. 1 and FIG. 2. The results for the TNP-specific DTH reaction system is given in Table 1.

In the test results, significant difference in the average values from the control was calculated by means of the Student's t-test and is expressed with asterisks (*: $p<0.05$; : $p<0.01$; *: $p<0.001$).

TABLE 1

| Tested Compound | Swelling in Paws ($\times 10^{-2}$ mm) | |
|---|---|---|
| | After 24 Hrs. | After 48 Hrs. |
| Not Sensitized | 11.7 ± 3.8*** | 10.0 ± 2.8* |
| Control | 49.2 ± 3.5 | 21.7 ± 3.8 |
| Product of this Invention | 26.7 ± 4.4** | 10.8 ± 2.4* |
| Cyclosporin | 15.8 ± 2.0*** | 10.8 ± 2.7* |
| Cyclophosphamide | 13.3 ± 2.1*** | 15.8 ± 2.4 |
| Prednisolone | 30.0 ± 5.6* | 8.3 ± 3.3* |
| Levamizole | 40.0 ± 6.5 | 20.0 ± 5.0 |

II. INHIBITORY ACTION TO HYPEREOSINOPHILICITY

The inhibitory action to hypereosinophilicity was measured using a ragweed pollen antigen induced reaction and a platelet activating factor (PAF) reaction.

(1) Hypereosinophilic Model Induced by Ragweed Pollen Antigen.

A ragweed pollen extract (which was diluted to an extent of 1,000 times using a physiological saline solution) was hypodermically injected into female BALB/c mice of six to eight weeks age for sensitization at the dose of 0.1 ml on the initiation day and on the first day and 0.2 ml on the sixth, eighth and fourteenth days. On the twentieth day, 0.2 ml of a 1,000 times diluted ragweed antigen was intraperitoneally injected into the mice to induce the reaction. On the 24th hour after the induction, the peritoneal exudate cells were recovered and subjected to a Giemsa staining and the total cell numbers, number of eosinophils, number of neutrophils and number of mononuclear cells were counted. As a result, the number of the eosinophils peaked 24 hours after the induction. In the case of BALB/c nude mice having no T cells, no exudation to peritoneum was noted at all both in eosinophils and in neutrophils.

(2) Measurement of the Action of the Tested Pharmaceuticals.

The above-mentioned hypereosinophilic models were used for checking the action towards the hypereosinophilicity by a hypodermic injection of the product of the present invention. Thus, histamine-added mouse gamma-globulin, at a dose of 3 mg/mouse/day twice a week for three weeks was administered until the induced day. Further tests were conducted by administering the corresponding amount of each of histamine (dihydrochloride) and mouse gamma-globulin which are the constituting components of the histamine-added mouse gamma-globulin. In addition, cyclosporin A, which is known as an immuno-suppressive agent, was hypodermically administered at the dose of 100 mg/kg/day for three days from two days prior to the induction until the induced day and the results were used for comparison.

An example of the results is given in Table 2:

TABLE 2

| Tested Pharmaceuticals | Number of Eosinophils Exudated to Peritoneum ($\times 10^5$ cells) |
|---|---|
| Not Sensitized | 0.4 ± 0.1*** |
| Control | 3.7 ± 0.4 |
| Product of the Invention | 0.5 ± 0.1*** |
| Histamine | 3.4 ± 0.6 |
| gamma-Globulin | 3.2 ± 0.5 |
| Cyclosporin A | 0.4 ± 0.2*** |

(3) Measurement of the Action of the Tested Pharmaceuticals Using Hypereosinophilic Model Induced by Platelet Activating Factor (PAF).

A PAF (5 micrograms/200 microliters) was intraperitoneally injected into female BALB/c mice of six to eight weeks age to induce the reaction. After 24 hours from the induction, the peritoneal exudate cells were recovered and the number of the eosinophils were counted. The resulting hypereosinophilic model was used for checking the suppressive action of the product of the present invention (i.e., histamine-added mouse gamma-globulin) against the eosinophilicity in the same manner as mentioned above.

An example of the results is given in Table 3:

TABLE 3

| Tested Pharmaceutical | Number of Exudated Eosinophils to Peritoneum ($\times 10^5$ cells) |
|---|---|
| Not Sensitized | 0.3 ± 0.1** |
| Control | 2.3 ± 0.5 |
| Product of the Invention | 0.8 ± 0.1* |
| Histamine | 2.2 ± 0.8 |
| gamma-Globulin | 1.5 ± 0.2 |

It is clear from the results of FIG. 1 and FIG. 2 that the histamine-added gamma-globulin (the product of the present invention) exhibited significant promoting action upon IgG and IgM antibody production. However, cyclosporin A and cyclophosphamide (immunosuppressive agents) significantly suppressed the production of both antibodies. Prednisolone (an adrenocortical hormone) and levemizole (said to exhibit an immunomodulating action) did not significantly affect antibody production at the dose of the present test.

On the other hand, as shown in Table 1 the product of the present invention exhibited a significant suppressive action to the delayed type hypersensitivity (DTH). Both cyclosporin A and cyclophosphamide showed clear suppressive actions. In addition, prednisolone showed a weak suppressive action while levemisole had no significant effect.

As such, cyclosporin A and cyclophosphamide (conventional immunosuppressive agents) significantly suppressed the immunoreactions of both IgG and IgM antibody production and the DTH reaction. However, histamine-added gamma-globulin (the product of the present invention) exhibited a promoting action towards the antibody production and a suppressive action upon the DTH reaction. As such, the histamine-added gamma-globulin has an immunomodulating action which is clearly unexpectedly different from the action of conventional immunosuppressive agents.

Furthermore, as shown in Table 2, the product of the present invention significantly suppressed the eosinophil exudation into peritoneum in the hypereosinophilic model induced by a ragweed pollen antigen. Moreover, as apparent from the results of Table 3, the histamine-added gamma-globulin exhibited a clear suppressive action upon the hypereosinophilicity induced by administration of PAF instead of by an antigen induction like cyclosporin A which is an immunosuppressive agent. It is clear that said suppressive action upon hypereosinophilicity is an action which is specific to the product of the present invention because said action is not observed for each of the histamine and the gamma-globulin which are the components of the histamine-added gamma-globulin. Moreover, the product showed a significant suppressive action to the above-mentioned antigen-induced and PAF-induced hypereosinophilic models even in the same administration terms as for cyclosporin A (i.e., from two days before the induction until the induced day).

It is clear from the above-mentioned results of the pharmacological tests that the pharmaceutical composition of the present invention has a specific immunomodulating action which is unexpectedly different from the action of conventional immunosuppressive agents. Accordingly, said pharmaceutical composition is useful as a pharmaceutical agent for the therapy of diseases associated with an abnormal immune system such as chronic articular rheumatism, systemic lupus erythematosus, multiple sclerosis, etc. and various types of immunodeficiency syndromes. In addition, since the product of the present invention exhibits a suppressive action upon hypereosinophilicity, it can be used as a therapeutic agent for infectious diseases, parasitic diseases, respiratory diseases, autoimmune diseases and eosinophilia caused by malignant tumor, etc.

Eosinophils are known as effector cells which accumulate at the stimulated portion which causes inflammation and results in inflammatory symptoms. Accordingly, the agents which suppress the increase in eosinophils can be used as remedies for suppressing inflammation. The pharmaceutical composition of the present invention containing a histamine-added gamma-globulin exhibits an action of suppressing the tumor in the DTH reaction in addition to the above-mentioned suppressive action upon an increase in eosinophils. Accordingly, the composition is quite useful as an excellent antiinflammatory agent as well.

EXAMPLE 2

An example of a formulation of a pharmaceutical composition for treatment of humans according to the present invention is:

| Formulation | Components | Amount In a Vial |
|---|---|---|
| Injection (2 ml) | Histamine-Added Human gamma-Globulin | 36 mg |
| | Histamine Dihydrochloride | 0.45 microgram |
| | Sodium Chloride | q.s. |

The dose may be suitably selected depending upon the type of the disease, degree of the disease, age and sex of the patient, term of the administration, etc. to provide a pharmaceutically effective amount of the histamine-added human gamma globulin.

What is claimed is:

1. A method of treating an autoimmune disease except for autoimmune allergic skin diseases comprising administering a pharmaceutically effective amount of histamine-added gamma-globulin.

2. A method as claimed in claim 1 wherein the disease is multiple sclerosis.

3. A method as claimed in claim 1 wherein the disease is systemic lupus erythematosus.

4. A method as claimed in claim 1 wherein the disease is chronic articular rheumatism.

5. A method as claimed in claim 1 wherein said histamine-added gamma-globulin is obtained by admixing from about 1 to about 200 parts by weight of a gamma-globulin component with about 0.01 to about 2 parts by weight of a histamine component.

6. A method as claimed in claim 5 wherein said histamine-added gamma-globulin is obtained by admixing from about 5 to about 50 parts by weight of a gamma-globulin component with about 0.05 to about 0.5 parts by weight of a histamine component.

7. A method as claimed in claim 5 wherein said gamma-globulin component is human gamma-globulin.

8. A method as claimed in claim 5 wherein said histamine component is at least one pharmaceutically acceptable histamine salt.

9. A method as claimed in claim 8 wherein said salt is histamine dihydrochloride.

10. A method as claimed in claim 1 wherein said histamine-added gamma-globulin is formulated as a dry preparation for injection.

11. A method as claimed in claim 1 wherein said histamine-added gamma-globulin is solubilized for injection.

* * * * *

UNITED STATES PATENT AND TRADEMARK OFFICE
CERTIFICATE OF CORRECTION

PATENT NO. : 5,780,026
DATED : July 14, 1998
INVENTOR(S) : Haruo Yoshii; Yuriko Fukata It is certified that error appears in the above-identified patent and that said Letters Patent is hereby corrected as shown below:

In column 1 line 49, change "0.01" to --$0.01 \times 10^{-3}$--; on line 50, change "2" to --$.2 \times 10^{-3}$--; on line 52, change "0.05" to --$0.05 \times 10^{-3}$--; and on line 53, change "0.5" to --$0.5 \times 10^{-3}$--.

In column 2 line 19, change "0.01" to --$0.01 \times 10^{-3}$--, and change "2" to --$2 \times 10^{-3}$--; on line 22, change "0.05" to --$0.05 \times 10^{-3}$--, and change "0.5" to --$0.5 \times 10^{-3}$--; and line 25, change "100" to --1--.

<u>In the Claims</u>:

In claim 5 line 4, change "0.01 to about 2" to --$0.01 \times 10^{-3}$ to about $2 \times 10^{-3}$--.

In claim 6 line 4, change "0.05 to about 0.5" to --$0.05 \times 10^{-3}$ to about $0.5 \times 10^{-3}$--.

Signed and Sealed this

First Day of May, 2001

Attest:

NICHOLAS P. GODICI

*Attesting Officer*   *Acting Director of the United States Patent and Trademark Office*